United States Patent [19]

Michelotti et al.

[11] Patent Number: 5,304,572
[45] Date of Patent: Apr. 19, 1994

[54] N-ACETONYLBENZAMIDES AND THEIR USE AS FUNGICIDES

[75] Inventors: Enrique L. Michelotti, Fort Washington; David H. Young, Ambler, both of Pa.

[73] Assignee: Rohm and Haas Company, Philadelphia, Pa.

[21] Appl. No.: 984,137

[22] Filed: Dec. 1, 1992

[51] Int. Cl.$^5$ .................. A01N 47/46; A01N 47/48; C07C 331/12; C07C 331/20

[52] U.S. Cl. .................. 514/514; 514/522; 514/617; 514/622; 558/14; 558/17; 558/415; 564/176; 564/186

[58] Field of Search .................. 558/14, 17, 415; 564/176, 186; 514/514, 522, 617, 622

[56] References Cited

U.S. PATENT DOCUMENTS

| | | | |
|---|---|---|---|
| 3,551,484 | 12/1970 | Lewis et al. | 260/558 |
| 3,661,991 | 5/1972 | McNutty et al. | 260/558 D |
| 3,709,897 | 1/1973 | McNutty et al. | 260/307 F |
| 3,723,452 | 3/1973 | McNutty et al. | 260/307 F |
| 3,751,239 | 8/1973 | McNutty et al. | 71/118 |
| 3,819,355 | 6/1974 | McNutty et al. | 71/88 |
| 4,822,902 | 4/1989 | Carley et al. | 558/14 |

Primary Examiner—Richard L. Raymond
Attorney, Agent, or Firm—Kevin E. McVeigh

[57] ABSTRACT

Novel N-acetonylbenzamides and their use in controlling phytopathogenic fungi.

30 Claims, No Drawings

N-ACETONYLBENZAMIDES AND THEIR USE AS FUNGICIDES

BACKGROUND

The present invention relates to certain N-acetonyl-substituted benzamides and their use in controlling fungi, particularly phytopathogenic fungi.

It is known that benzamides of the class of N-(1,1-dialkyl-3-chloroacetonyl)substituted benzamides exhibit fungicidal activity, see, e.g. U.S. Pat. Nos. 3,661,991 and 3,751,239. The practical value of such compounds in the treatment of fungal infections of plants is limited by the substantial phytotoxicity also exhibited by the compounds. It has been recognized that the phytotoxicity of such N-acetonyl substituted benzamides can be reduced by altering the substituents on the terminal carbon to other than only hydrogen or chlorine, see, e.g. U.S. Pat. Nos. 4,822,902 and 4,863,940.

DESCRIPTION OF THE INVENTION

Phytopathogenic fungi are controlled by application of a fungicidally effective amount of compounds of the formula (1):

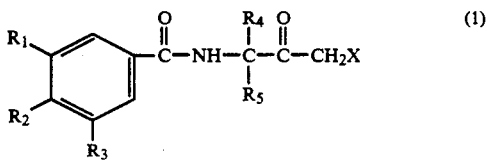

wherein:
- $R_1$ and $R_3$ are each independently halo or $(C_1-C_4)$alkyl;
- $R_2$ is $(C_1-C_4)$alkyl, $(C_2-C_4)$alkenyl, $(C_2-C_6)$alkynyl, $(C_1-C_4)$alkoxy or cyano;
- $R_4$ and $R_5$ are independently H or $(C_1-C_4)$alkyl, provided that at least one of $R_4$, $R_5$ is $(C_2-C_4)$alkyl; and
- X is halo, thiocyano or isothiocyano; or an agronomically acceptable salt thereof.

$(C_1-C_4)$alkyl is a straight or branched alkyl group having one to four carbon atoms per group and includes methyl, ethyl, n-propyl, iso-propyl, n-butyl, isobutyl, sec-butyl and tert-butyl.

$(C_2-C_4)$alkenyl is a straight or branched alkenyl group having two to four carbon atoms per group and includes, e.g., ethenyl, 2-propenyl, 2-butenyl, 1-methylethenyl, 2-methyl-2-propenyl.

$(C_2-C_6)$alkynyl is a straight or branched alkynyl group having from two to six carbons per group and includes, e.g., ethynyl, 2-propynyl, 2-butynyl.

Halo includes chloro, fluoro, bromo and iodo.

$(C_1-C_4)$alkoxy is a straight or branched alkoxy group having one to four carbon atoms per group and includes, e.g., methoxy, ethoxy, propoxy, isopropoxy, butoxy, isobutoxy, sec-butoxy and tert-butoxy.

Agronomically acceptable salts include, e.g., metal salts such as sodium, potassium, calcium and magnesium salts, ammonium salts such as isopropyl ammonium salts and trialkylsulfonium salts such as triethylsulfonium salts.

In a preferred embodiment, $R_1$ and $R_3$ are each independently chloro, fluoro, or bromo, $R_2$ is $(C_1-C_4)$alkyl, $(C_1-C_4)$alkoxy or cyano and X is chloro.

In a highly preferred embodiment, $R_1$ and $R_2$ are each chloro, $R_2$ is $(C_1-C_4)$alkyl, $(C_1-C_4)$alkoxy or cyano, $R_4$ is ethyl, $R_5$ is methyl and X is chloro.

The compounds of the present invention are useful in controlling phytopathogenic fungi, particularly fungi of the class Oomycetes, and exhibit high fungicidal activity and relatively low phytotoxicity. Important genera of the Oomycetes include Phytophthora, Plasmopara, Peronospora and Pseudoperonospora which cause diseases such as potato and tomato late blight, and downy mildew in grapes and other crops.

The compounds of the present invention can be applied as fungicidal sprays by methods commonly employed, such as conventional high-gallonage hydraulic sprays, low-gallonage sprays, air-blast, aerial sprays and dusts. The dilution and rate of application will depend upon the type of equipment employed, the method and frequency of application desired and diseases to be controlled, the effective amount is typically from about 0.01 kilogram (kg) compound per hectare to about 20 kg compound per hectare, preferably from about 0.1 kg compound per hectare to about 5 kg compound per hectare and more preferably from about 0.125 kg compound per hectare to about 0.5 kg compound per hectare.

The compounds of the present invention are useful for the control of phytopathogenic fungi on crops and may be used as seed protectants, soil fungicides and/or foliar fungicides. As a seed protectant, a compound of the present invention is coated on seed at a dosage rate of about 10 grams (g) compound per 50 kg seed to about 20 g compound per 50 kg seed. As a soil fungicide, a compound of the present invention can be incorporated in the soil or applied to the surface of the soil at a dosage rate of about 0.5 kg compound per hectare to about 20 kg compound per hectare and preferably at a rate of about 1 kg compound per hectare to about 5 kg compound per hectare. As a foliar fungicide, a compound of the present invention is applied to growing plants at a dosage rate of about 0.1 kg compound per hectare to about 5 kg compound per hectare and preferably at a rate of about 0.125 kg compound per hectare to about 0.5 kg compound per hectare.

For the above disclosed purposes these compounds can be used in the technical or pure form as prepared, as solutions or as formulations. The compounds are usually taken up in a carrier or are formulated so as to render them suitable for subsequent use as fungicides. For example, the compounds can be formulated as wettable powders, dry powders, emulsifiable concentrates, dusts, granular formulations, aerosols, or flowable emulsion concentrates. In such formulations, the compounds are extended with a liquid or solid carrier and, when dried, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in *McCutcheon's Emulsifiers and Detergents, McCutcheon's Emulsifiers and Detergents/Functional Materials and McCutcheon's Functional Materials* all published annually by McCutcheon Division of MC Publishing Company (New Jersey).

In general, the compounds utilized in this invention can be dissolved in appropriate solvents such as acetone, methanol, ethanol, dimethylformamide or dimethyl sulfoxide and such solutions extended with water. The concentrations of the solution can vary from 1% to 90% with a preferred range being 5% to 50%.

For the preparation of emulsifiable concentrates, the compounds used in the invention can be dissolved in suitable organic solvents or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%. Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%.

Dusts are prepared by mixing the compounds of the present invention salts and complexes thereof with finely divided inert solids which can be organic or inorganic in nature. Inert materials useful for this purpose include botanical flours, silicas, silicates, carbonates and clays. One convenient method of preparing a dust is to dilute a wettable powder with a finely divided carrier. Dust concentrations containing 20% to 80% of the active ingredient are commonly made and are subsequently diluted to 1% to 10% use concentration.

The compounds of the present invention can also be utilized in combination with other fungicides such as:

(a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)s-triazine, diethyl phthalimidophosphorothioate, 4-butyl-1,2,4-triazole, 5-amino-1-[bis(dimethylamino)phosphinyl]-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-[4,5-b]quinoxaline-2-thione (thioquinox), ethyl 1-(butylcarbamoyl)-2-benzimidazole carbamate (benomyl), 2-4'-(thiazolyl) benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-dichlorophenoxy)-alpha-(1,1-dimethylethyl)-1H-1,2,4-triazole-1-ethanol (triadimenol); 1-(4-chlorophenoxy)-3,3-dimethyl-1-(1H-1,2,4-triazol-1-yl)-2-butanone (triadimefon); beta-[1,1'-biphenyl)-4-yloxyl]-alpha-(1,1-dimethylethyl)-1H-1,2,4-triazole-1-ethanol (bitertanol); 2,3-dichloro-N-(4-fluorophenyl)maleimide (fluoroimide); 1-[2-(2,4-dichlorophenyl)-4-propyl-1,3-dioxolan-2-ylmethyl]-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha-(phenyl)-alpha-(2,4-dichlorophenyl)-5-pyrimidinylmethanol (triarimol), cis-N-[1,1,2,2-tetrachloroethyl)thio]-4-cyclohexene-1,2-dicarboximide, 3-[2-(3,5-dimethyl-2-oxycyclohexyl)-2-hydroxy]glutarimide (cycloheximide), dehydroacetic acid, N-(1,1,2,2-tetrachloroethylthio)-3a,4,7,7a-tetrahydrophthalimide (captafol), butyl-2-ethylamino-4-hydroxy-6-methylpyrimidine (ethirimol), acetate of 4-cyclodecyl-2,6-dimethyl-morpholine (dodemorph), 4-[3-(4-chlorophenyl)-3-(3,4-dimethoxyphenyl)acryloyl]morpholine (dimethomorph) and 6-methyl-2-oxo-1,3-dithiolo[4,5-b]-quinoxaline (quinomethionate).

(d) miscellaneous halogenated fungicides such as: tetrachloro-p-benzoquinone (chloranil), 2-3-dichoro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as pentachloronitrobenzene (PCNB) and tetrafluorodichloroacetone;

(e) fungicidal antibiotics such as: griseofulvin, kasugamycin and streptomycin;

(f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sulfone, dodecylguanidine acetate (dodine), aluminum tris-o-ethyl phosphonate(fosetyl-al), N-(2,6-dimethylphenyl)-N-(methoxyacetyl)alanine methyl ester(methoxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, 1,2-bis(3,-methoxycarbony-2-thioureido) benzene (thiophanate-methyl), and 2-cyano-N-(ethylamino)carbonyl)-2-(methoxyimine)acetamide (cymoxanil).

The benzamide compounds of the present invention can be prepared using conventional synthesis techniques, as shown in scheme A. For example, compounds of formula (I) can be prepared by treating acetylenic amides (II) with a halogen or a halogen source at a temperature of −20° C. in the presence of a solvent such as methylene chloride, to give an intermediate oxazoline (III) which is readily hydrolyzed under acidic conditions using hydrochloric acid and methanol or tetrahydrofuran as solvent at a temperature of 40° C. to 50° C. The starting acetylenic amides can be prepared by reaction of the corresponding aromatic acyl chloride (IV) and an acetylenic amine (V) in the presence of a base such as sodium hydroxide, triethylamine or pyridine using water, methylene chloride or ethyl ether as a solvent at room temperature.

SCHEME A

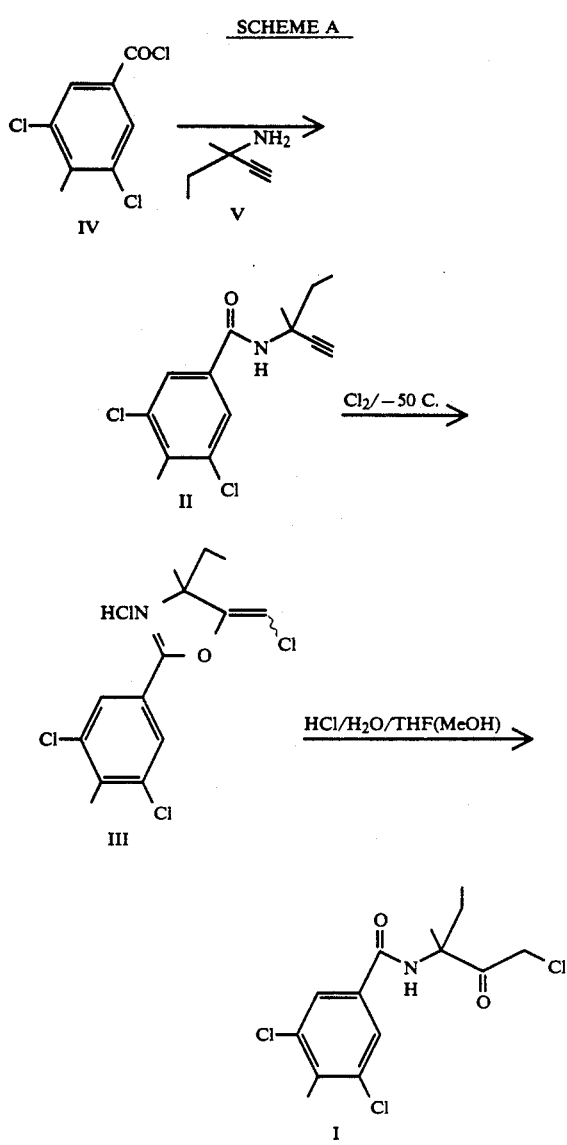

The acetylenic amine (V) can be prepared from the corresponding commercially available acetylenic alcohol (VI), as shown in Scheme B.

SCHEME B

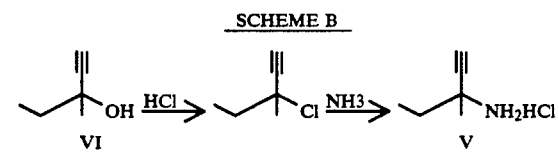

Synthesis techniques for making exemplary benzoyl chloride starting materials (IV) are outlined below in Schemes C and D.

SCHEME C

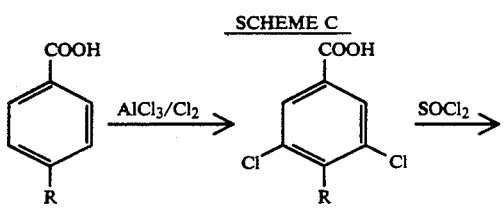

SCHEME C -continued

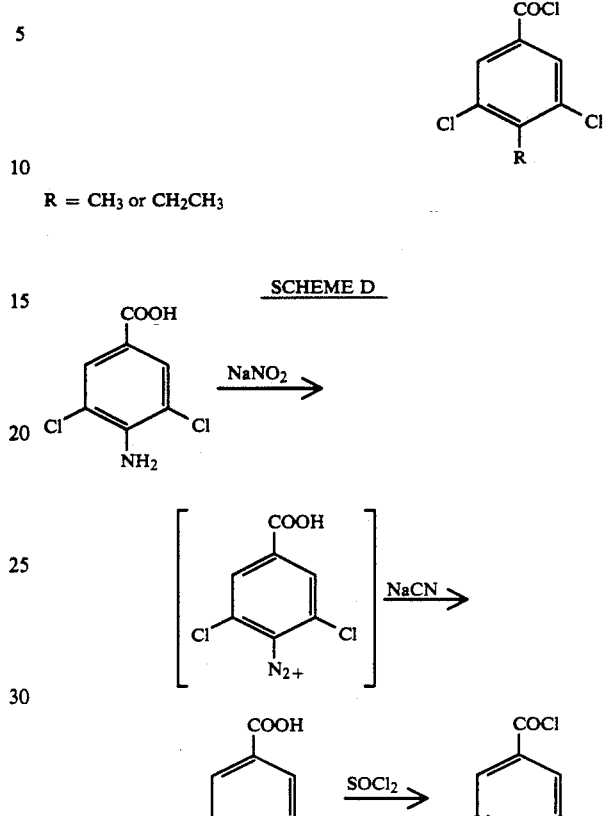

R = CH₃ or CH₂CH₃

SCHEME D

EXAMPLE 1:

N-[3'-(1'-chloro-3'-methyl-2'-oxopentan]-3,5-dichloro-4-methylbenzamide

Step a) Preparation of 3,5-dichloro-4-methylbenzoic acid:

To a solution of p-toluic acid (95.0 g, 0.698 mole) in methylene chloride (1 liter), was added aluminum chloride (260.0 g, 1.948 mole), portionwise, while keeping the reaction temperature below 10° C. When the addition was completed, chlorine gas was bubbled in at such a rate as to keep the temperature below 10° C. The reaction was followed by GLC. After about 4 hours most of the starting material had been converted to the expected compound. The resulting mixture was poured into ice and concentrated hydrochloric acid, and then extracted with ethyl acetate several times. The combined organic layers were washed with water and then dried over anhydrous sodium sulfate. Removing the solvent in the rotavap yielded the crude product as a white solid. Recrystalization from acetone/water yielded 3,5-dichloro-4-methylbenzoic acid with minor impurities 115.4 g (81% yield of product).

Step b) Preparation of 3,5-dichloro-4-methylbenzoyl chloride:

A mixture of 3,5-dichloro-4-methylbenzoic acid (230 g, 1.12 moles), thionyl chloride (204 g, 1.71 moles), and dimethylformamide (30 milliliters(ml), in toluene (1 liter) was slowly warmed to 70° C. and stirred at that temperature for 2 hours. The toluene was eliminated in the rotavap to yield 276 g of 3,5-dichloro-4-methylbenzoyl chloride, used in the next step as such.

Step c) Preparation of 3-methyl-1-pentyn-3-amine

In a 2000 ml, four-necked, round-bottomed flask fitted with a thermometer in a side-armed adapter connected to a scrubbing system, a mechanical stirrer, a 500 ml addition funnel and a bubbling tube connected to a lecture bottle of hydrogen chloride gas, were placed 350 ml of concentrated hydrochloric acid. This solution was cooled to 5° C., and hydrogen chloride gas was bubbled in until the size of the bubbles were constant. To this the alcohol was added at such a rate as to keep the temperature below 0° C., while simultaneously bubbling hydrogen chloride gas through the reaction mixture. The addition took between 2 to 2.5 hours. After the addition of the alcohol was complete the resulting mixture was stirred at −5° C. for an additional 30 to 45 minutes. The resulting layers were separated and the organic layer was washed with ice-water until the pH of washing liquids was 7. The resulting light yellow mobile oil was used in the following step without further purification.

Step d) Preparation of 3-amino-3-methyl-1-pentyne.

In a 3000 ml, four-necked, round-bottomed flask fitted with a thermometer in a side-armed adapter connected to a scrubbing system, a mechanical stirrer, a 500 ml addition funnel and a bubbling tube connected to a lecture bottle of $NH_3$ gas, was placed 1000 ml of concentrated ammonium hydroxide. This solution was cooled to −5° C., and $NH_3$ gas was bubbled in until the size of the bubbles was constant. To this the chloride (600 g) and the 50% NaOH were charged in the addition funnels and added to the ammonia solution at such a rate that equal stoichiometric amounts of each compound were introduced into the reaction flask and that the temperature was kept below 0° C. The addition took 2 to 3 hours. After the addition was complete, the reaction mixture was stirred 1 hour at −5° C. The phases were separated and the organic phase was washed once with ice-water. The light yellow oil obtained was codistilled with water at atmospheric pressure. Four fractions were separated:

Fraction 1 (bp 71° to 79° C.) included amine plus low boiling olefins.

Fraction 2 and 3 (bp 80° to 85° C. and 85° to 89° C.) were pure amine by 1H-NMR (total 220 g).

Fraction 4 (bp 90° to 99° C.) was a mixture of the amine and the starting alcohol.

Fractions 1 and 4 were combined and dissolved in dry ether, with hydrogen chloride gas bubbled in while cooling. In this way 90 g of the pure amine hydrochloride was obtained. Total yield from the alcohol was 57%.

Step e) Preparation of N-[3'-(3'-methyl-1'-pentynyl)]-3,5-dichloro-4-methylbenzamide:

In a 2 liter, three-necked, round-bottomed flask fitted with a mechanical stirrer, nitrogen inlet and thermometer were placed 142 g of 3-methyl-1-pentyn-3-amine hydrochloride, 300 ml of tetrahydrofuran and 350 ml of dimethylformamide. To the resulting well stirred mixture was added slowly 212 ml of triethylamine, keeping the temperature between 5° to 10° C. To the resulting mixture was added 221 g of the preceding acyl chloride at such a rate to keep the reaction temperature at 5° to 10° C. After the addition was complete, the reaction mixture was stirred at room temperature for 3 hours, poured into 2 liters of water and extracted with ethyl acetate (3×400 ml). The combined organic layers were washed with water (1×300 ml), then with 5% aqueous hydrochloric acid (2×300 ml), then with water (1×300 ml), then with 5% aqueous sodium carbonate (2×300 ml) and then again with water (2×300 ml), then dried over anhydrous sodium sulfate. The solvent was removed in the rotavap yielding 266 g of N-[3'-(3'-methyl-1'-pentynyl)]-3,5-dichloro-4-methylbenzamide.

Step f) Preparation of 2-(3,5-dichloro-4-methylphenyl)-4-methyl-4-ethyl-5-chloromethylenyloxazoline In a 3 liter, three-necked, round-bottomed flask fitted with a mechanical stirrer, a thermometer and a 100 ml addition funnel was dissolved 143 g, 0.503 mole of N-[3'-(3'-methyl-1'-pentynyl)]-3,5-dichloro-4-methylbenzamide in 750 ml of methylene chloride. The resulting mixture was cooled down to −50° C. and a cold chlorine solution in methylene chloride (800 ml, 0.528M) was added very slowly. When the addition was completed, the reaction mixture was stirred at −65° C. for 30 minutes. The crude reaction mixture was evaporated in the rotavap yielding 168.5 g of 2-(3,5-dichloro-4-methylphenyl)-4-methyl-4-ethyl-5-chloromethylenyloxazoline as a light yellow solid which was used as such in the next step.

Step g) Preparation of N-[3'-(1'-chloro-3'-methyl-2'-oxopentan)]-3,5-dichloro-4-methylbenzamide:

168 g, 0.473 moles, of 2-(3,5-dichloro-4-methylphenyl)-4-methyl-4-ethyl-5-chloromethylenyloxazoline prepared in the preceding step was dissolved in 1.6 liters of tetrahydrofuran, 250 ml of water, and 60 ml of concentrated hydrochloric acid, warmed to 55° C. and stirred at that temperature for four hours. The crude reaction mixture was cooled down and poured into a mixture of ice and water and then extracted with methylene chloride (4×400 ml). The combined organic layers were washed with brine, and then dried. The solvent was evaporated in the rotavap yielding the N-[3'-(1'-chloro-3'-methyl-2'-oxopentan)]-3,5-dichloro-4-methylbenzamide.

EXAMPLE 2

N-[3'-(1'-chloro-3'-methyl-2'-oxopentan]-3,5-dichloro-4-ethylbenzamide

This compound was prepared by the method set forth above in Example 1 starting with 4-ethylbenzoic acid.

EXAMPLE 3

N-[3'-(1'-chloro-3'-methyl-2'-oxopentan]-3,5-dichloro-4-ethoxybenzamide, and

EXAMPLE 4

N-[3'-(1'-chloro-3'-methyl-2'-oxopentan]-3,5-dichloro-4-methoxybenzamide

The compounds of Examples 3 and 4 were prepared by the method set forth above in Example 1 starting with 3,5-dichloro-4-hydroxybenzoic acid, from which the ethyl and methyl ether derivatives were made.

EXAMPLE 5

N-[3'-(1'-chloro-3'-methyl-2'-oxopentan)]-4-cyano-3,5-dichlorobenzamide

Step a) Preparation of 4-cyano-3,5-dichlorobenzoic acid

In a 100 ml round-bottomed flask was placed 25 ml of concentrated sulfuric acid, cooled down to 5° C. To this well stirred liquid was added 3.82 g (0.055 mole) of sodium nitrite. The resulting mixture was warmed to 50° C. until a solution was obtained (approx 30 minutes).

The resulting solution was cooled down to 0° C. (ice-bath). 10.0 g (0.049 mole) of 4-amino-3,5-dichlorobenzoic acid were added to the solution portion-wise, over a 45 minute period, with vigorous stirring, all the while keeping the temperature between 3° to 5° C. After the addition was complete, the resulting mixture was allowed to warm up to 15° C. and was then stirred at that temperature for 90 minutes. The mixture was then poured into a mixture of 17.3 g (0.26 mol) potassium cyanide in 50 ml of water at 15° C. with vigorous stirring. The resulting mixture was warmed up to 35°-40° C. for 40 minutes, then cooled to room temperature and then extracted with ethyl acetate. The combined organic layers were washed with water, and then dried over anhydrous magnesium sulfate. The solvent was then removed in the rotavap, yielding 4.07 g of N-[3'-(1'-chloro-3'-methyl-2'-oxopentan)]-4-cyano-3,5-dichlorobenzamide. This compound was used as such in the next step.

Step b) 4-cyano-3,5-dichlorobenzoyl chloride

To 4-cyano-3,5-dichlorobenzoic acid (4.07 g, 0.019 mol) dissolved in 100 ml of dry toluene were added thionyl chloride (1.4 ml, 0.019 mol) and dimethylformamide (2 drops). The resulting mixture was refluxed during 3 hours, cooled down to room temperature and the solvent eliminated in the rotavap. The residue was dried under vacuum and used as such in the following step.

Step c) N-[3'-methyl-1'-pentynyl)]-4-cyano-3,5-dichlorobenzamide

To a well stirred mixture of 4-cyano-3,5-dichlorobenzoyl chloride (4.0 g, 0.017 mol) and water (100 ml) at 0° C. (ice-water bath) were added 3-amino-3-methyl-1-pentyne hydrochloride and 50 weight percent aqueous sodium hydroxide (10 ml). The resulting mixture was stirred 1 hour at 0° C., warmed up to room temperature and extracted with ethyl acetate (3×50 ml), the combined organic layers were washed with water (3×50 ml), and then dried over anhydrous sodium sulfate. The solvent was then eliminated in the rotavap, yielding the crude product as a yellow oil (2.79 g). The crude product was purified by Michel-Miller chromatographic column packed with Merck (grade 60) silica gel using ethyl acetate as solvent, yielding 0.75 g of N-[3'-methyl-1'-pentynyl)]-4-cyano-3,5-dichlorobenzamide.

Step d) Preparation of 2-(4-cyano-3,5-dichlorophenyl)-4-methyl-4-ethyl-5-chloromethylenyloxazoline In a 50 ml, three-necked, round-bottomed flask fitted with a magnetic stirrer, a thermometer and a 10 ml addition funnel were dissolved 0.5 g (1.7 millimoles) of N-[3'-(3'-methyl-1'-pentynyl)]-4-cyano-3,5-dichlorobenzamide in 25 ml methylene chloride. The resulting mixture was cooled down to −50° C. and a cold chlorine solution in methylene chloride (1.7 ml, 1.0M) was added very slowly. When the addition was completed, the reaction mixture was stirred at −65° C. for 30 minutes. The solvent was evaporated from the crude reaction mixture in the rotavap yielding 2-(4-cyano-3,5-dichlorophenyl)-4-methyl-4-ethyl-5-chloromethylenyloxazoline as a light yellow solid which was used as such in the next step.

Step e) Preparation of N-[3'-(1'-chloro-3'-methyl-2'-oxopentan)]-4-cyano-3,5-dichlorobenzamide The crude product from the preceding step was dissolved in a 50 mL of methanol, 2 ml of water, and 3 ml of concentrated hydrochloric acid, warmed up to 55° C. and stirred at that temperature during four hours. The crude reaction mixture was cooled down and poured into a mixture of ice and water, then neutralized with saturated aqueous sodium bicarbonate and then extracted with methylene chloride (4×50 ml). The combined organic layers were washed with brine and then dried. The solvent was evaporated in the rotavap, yielding the crude product, which was purified by column chromatography yielding 120 mg of N-[3'-(1'-chloro-3'-methyl-2'-oxopentan)]-4-cyano-3,5-dichlorobenzamide.

Exemplary compounds of the present invention are set forth in Table 1.

TABLE 1

N-acetonylbenzamides of the structural formula:

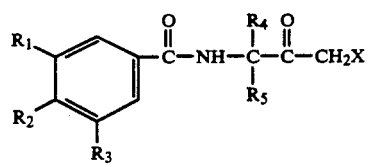

| Ex. No. | $R_1$ | $R_2$ | $R_3$ | $R_4$ | $R_5$ | X |
|---|---|---|---|---|---|---|
| 1 | Cl | $CH_3$ | Cl | $CH_2CH_3$ | $CH_3$ | Cl |
| 2 | Cl | $CH_2CH_3$ | Cl | $CH_2CH_3$ | $CH_3$ | Cl |
| 3 | Cl | $OCH_2CH_3$ | Cl | $CH_2CH_3$ | $CH_3$ | Cl |
| 4 | Cl | $OCH_3$ | Cl | $CH_2CH_3$ | $CH_3$ | Cl |
| 5 | Cl | CN | Cl | $CH_2CH_3$ | $CH_3$ | Cl |

Characterization of each of the compounds of Examples 1-5 with respect to their NMR spectra is provided below in Table 2.

TABLE 2

| Example Number | 200 MHz, delta scale in ppm, Tetramethylsilane (TMS) standard, solvent $CDl_3$ |
|---|---|
| 1. | 7.70(2, s), 6.80(1, s), 4.40(2, d), 2.50(3, s), 1.65 (2, s), 1.60(3, s), 0.90(3, t) |
| 2. | 7.70(2, s), 6.75(1, bs), 4.35(2, c), 2.95(2, c), 2.40-2.10(1, m), 2.10-1.80(1, m), 1.65(3, s), 1.20(3, t), 0.85(3, t) |
| 3. | 7.70(2, s), 6.90(1, bs), 4.40(2, c), 4.15(2, c), 2.40-2.10(1, m), 2.10-1.80(1, m), 1.60(3, s), 1.45(3, t), 0.90(3, t) |
| 4. | 7.75(2, s), 6.90(1, bs), 4.40(2, c), 3.95(3, s), 2.40-2.10(1, m), 2.10-1.80(1, m), 1.65(3, s), 0.90(3, t) |
| 5. | 7.85(1, s), 7.15(1, bs), 4.40(2, c), 2.50-2.30 2.00-1.80(1, m), 1.70(3, s), 0.90(3, t) |

EXAMPLE 6

The compounds of Examples 1-5 were tested for fungicidal activity and phytoxicity and compared to results obtained with the compounds of Comparative Examples C1-C4 set forth below in Table 3.

TABLE 3

N-acetonylbenzamides of the structural formula:

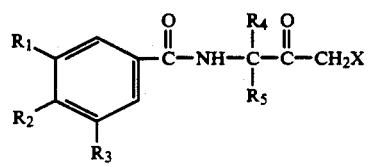

| Ex. No. | $R_1$ | $R_2$ | $R_3$ | $R_4$ | $R_5$ | X |
|---|---|---|---|---|---|---|
| C1 | Cl | OH | Cl | $CH_3$ | $CH_3$ | Cl |
| C2 | Cl | $CH_3$ | Cl | $CH_3$ | $CH_3$ | Cl |
| C3 | Cl | H | Cl | $CH_2CH_3$ | $CH_3$ | Cl |

TABLE 3-continued

N-acetonylbenzamides of the structural formula:

$$R_1\text{-}\underset{R_2,R_3}{\text{(aryl)}}\text{-}\underset{\text{O}}{\overset{\text{O}}{\text{C}}}\text{-NH-}\underset{R_5}{\overset{R_4}{\text{C}}}\text{-}\overset{\text{O}}{\text{C}}\text{-CH}_2X$$

| Ex. No. | $R_1$ | $R_2$ | $R_3$ | $R_4$ | $R_5$ | X |
|---|---|---|---|---|---|---|
| C4 | Cl | Cl | Cl | $CH_2CH_3$ | $CH_3$ | Cl |

Fungitoxicity Assay against Pythium Ultimum

Dilution series of the compounds of Examples 1–5 and Comparative Examples C1–C4 were prepared in dimethylsulfoxide, and 0.1 ml of each dilution was added to 19.9 ml of a liquid asparagine-sucrose medium (see, Erwin, D. C. and Katznelson, K., 1971, Can. J. Microbiol. 7, 15) in 9 cm diameter petri dishes to give the desired concentrations of test compound. Each plate was inoculated with a mycelial plug, 7 mm diameter, taken from the growing edge of a culture of *Pythium ultimum* grown on potato dextrose agar. Two replicate plates were used for each treatment. The increase in mycelial dry weight was determined after growth for 48 hours at 25° C. with shaking on a gyrotary shaker at 60 revolutions per minute. Pythium EC50 values were calculated from dose response curves. As used herein, the terminology "EC50" means the concentration of test compound required to inhibit growth by 50% as compared to a control lacking the test compound.

Phytotoxicity Assay

Dilution series of the compounds of Examples 1–5 and C1–C4 were prepared in dimethylsulfoxide and 20 microliters (µl) of each dilution was added to 20 ml of molten nutrient medium, consisting of Murashige and Skoog salt base, 2% sucrose and 1% agar, to give the desired concentrations of test compound. The mixtures were poured immediately into 9 cm diameter petri dishes. Surface-sterilized tobacco seeds were placed on each plate (20 seeds per plate) and the plates incubated in a vertical position in a 27° C. incubator with a 16 hour photoperiod. After 7 days the mean root lengths were calculated. Tobacco EC50 values were determined from dose response curves.

The ratio of Pythium EC50 value to tobacco EC50 value was calculated for each compound to provide an index of the fungicidal activity relative to the phytotoxicity for each compound.

Results of the fungitoxicity and phytotoxicity assays are set forth in Table 4 as "Pythium EC50" and "Tobacco EC50", each in units of micrograms per milliliter (µg/ml) and "(Pythium EC50/Tobacco EC50)", i.e. the ratio of the Pythium EC50 value to the Tobacco EC50 value, obtained for each compound.

TABLE 4

| Example No. | Pythium EC50 (µg/ml) | Tobacco EC50 (µg/ml) | (Pythium EC50/ Tobacco EC50) |
|---|---|---|---|
| 1 | 0.02 | 0.05 | 0.4 |
| 2 | 0.12 | 0.22 | 0.55 |
| 3 | 0.49 | 1.58 | 0.31 |
| 4 | 0.14 | 0.25 | 0.56 |
| 5 | 0.11 | 0.48 | 0.23 |
| C1 | 10.7 | >20 | <0.53 |
| C2 | 0.09 | 0.03 | 3 |
| C3 | 0.011 | 0.004 | 2.75 |
| C4 | 0.08 | 0.05 | 1.6 |

The compounds of Examples 1–5 provide a combination of high fungicidal activity and relatively low phytotoxicity while compounds of Comparative Examples C1–C4 each provide either a combination of low phototoxicity and low fungicidal activity, e.g. Comparative Example C1, or a combination high fungicidal activity and relatively high phytotoxicity, e.g. Comparative Example C4.

What is claimed is:

1. A compound of the formula:

$$R_1\text{-}\underset{R_2,R_3}{\text{(aryl)}}\text{-}\underset{\text{O}}{\overset{\text{O}}{\text{C}}}\text{-NH-}\underset{R_5}{\overset{R_4}{\text{C}}}\text{-}\overset{\text{O}}{\text{C}}\text{-CH}_2X$$

wherein, $R_1$ and $R_3$ are each independently halo or $(C_1-C_4)$ alkyl;

$R_2$ is $(C_1-C_4)$alkyl, $(C_2-C_4)$alkenyl, $(C_2-C_6)$alkynyl, $(C_1-C_4)$alkoxy, or cyano;

$R_4$ and $R_5$ are each independently $(C_1-C_4)$alkyl, provided that at least one of $R_4$, $R_5$ is $(C_2-C_4)$alkyl; and X is halo, thiocyano or isothiocyano;

or an agronomically acceptable salt thereof.

2. The compound of claim 1, wherein $R_1$ and $R_3$ are each independently chloro, fluoro or bromo; $R_2$ is $(C_1-C_4)$alkyl, $(C_1-C_4)$alkoxy or cyano; and X is chloro.

3. The compound of claim 2, wherein $R_1$ and $R_3$ are each chloro, fluoro or bromo.

4. The compound of claim 3, wherein $R_1$ and $R_3$ are each chloro.

5. The compound of claim 4, wherein $R_4$ is ethyl and $R_5$ is methyl.

6. The compound of claim 4, wherein $R_2$ is $(C_1-C_4)$alkyl.

7. The compound of claim 6 wherein $R_2$ is methyl or ethyl.

8. The compound of claim 4, wherein $R_2$ is $(C_1-C_4)$alkoxy.

9. The compound of claim 8 wherein $R_2$ is methoxy or ethoxy.

10. The compound of claim 4, wherein $R_2$ is cyano.

11. A fungicidal composition comprising an agronomically acceptable carrier and a fungicidally effective amount of the compound of claim 1.

12. A fungicidal composition comprising an agronomically acceptable carrier and a fungicidally effective amount of the compound of claim 2.

13. A fungicidal composition comprising an agronomically acceptable carrier and a fungicidally effective amount of the compound of claim 3.

14. A fungicidal composition comprising an agronomically acceptable carrier and a fungicidally effective amount of the compound of claim 4.

15. A fungicidal composition comprising an agronomically acceptable carrier and a fungicidally effective amount of the compound of claim 5.

16. A fungicidal composition comprising an agronomically acceptable carrier and a fungicidally effective amount of the compound of claim 6.

17. A fungicidal composition comprising an agronomically acceptable carrier and a fungicidally effective amount of the compound of claim 7.

18. A fungicidal composition comprising an agronomically acceptable carrier and a fungicidally effective amount of the compound of claim 8.

19. A fungicidal composition comprising an agronomically acceptable carrier and a fungicidally effective amount of the compound of claim 9.

20. A fungicidal composition comprising an agronomically acceptable carrier and a fungicidally effective amount of the compound of claim 10.

21. A method for controlling phytopathogenic fungi, comprising applying a fungicidally effective amount of the compound of claim 1 to plant foliage, plant seed or to a growth medium therefore.

22. A method for controlling phytopathogenic fungi, comprising applying a fungicidally effective amount of the compound of claim 2 to plant foliage, plant seed or to a growth medium therefore.

23. A method for controlling phytopathogenic fungi, comprising applying a fungicidally effective amount of the compound of claim 3 to plant foliage, plant seed or to a growth medium therefore.

24. A method for controlling phytopathogenic fungi, comprising applying a fungicidally effective amount of the compound of claim 4 to plant foliage, plant seed or to a growth medium therefore.

25. A method for controlling phytopathogenic fungi, comprising applying a fungicidally effective amount of the compound of claim 5 to plant foliage, plant seed or to a growth medium therefore.

26. A method for controlling phytopathogenic fungi, comprising applying a fungicidally effective amount of the compound of claim 6 to plant foliage, plant seed or to a growth medium therefore.

27. A method for controlling phytopathogenic fungi, comprising applying a fungicidally effective amount of the compound of claim 7 to plant foliage, plant seed or to a growth medium therefore.

28. A method for controlling phytopathogenic fungi, comprising applying a fungicidally effective amount of the compound of claim 8 to plant foliage, plant seed or to a growth medium therefore.

29. A method for controlling phytopathogenic fungi, comprising applying a fungicidally effective amount of the compound of claim 9 to plant foliage, plant seed or to a growth medium therefore.

30. A method for controlling phytopathogenic fungi, comprising applying a fungicidally effective amount of the compound of claim 10 to plant foliage, plant seed or to a growth medium therefore.

* * * * *